(12) United States Patent
Brown et al.

(10) Patent No.: US 6,743,209 B2
(45) Date of Patent: Jun. 1, 2004

(54) CATHETER WITH INTEGRAL ANCHORING MEANS

(76) Inventors: John Howell Brown, 303 Arnold Mill Rd., Woodstock, GA (US) 30188; Wallace Maurice Sumner, 1697 Hillside St., Marietta, GA (US) 30066-4194

( * ) Notice: Subject to any disclaimer, the term of this patent is extended or adjusted under 35 U.S.C. 154(b) by 0 days.

(21) Appl. No.: 10/193,890

(22) Filed: Jul. 12, 2002

(65) Prior Publication Data

US 2004/0010232 A1 Jan. 15, 2004

(51) Int. Cl.[7] .................... A61M 3/32; A61M 1/00; A01J 3/00; A01J 5/00
(52) U.S. Cl. .................... 604/174; 604/175; 604/327; 119/14.02
(58) Field of Search ............................. 604/714, 523, 604/500, 533, 93, 175, 327, 329, 331; 128/760, 761, 767, 768; 119/14.02

(56) References Cited

U.S. PATENT DOCUMENTS

| | | | |
|---|---|---|---|
| 2,127,903 A | | 8/1938 | Bowen |
| 3,730,187 A | | 5/1973 | Reynolds |
| 3,821,957 A | | 7/1974 | Riely |
| 4,057,066 A | | 11/1977 | Taylor |
| 4,230,110 A | | 10/1980 | Beroff |
| 4,392,854 A | | 7/1983 | Ibach |
| 4,650,473 A | | 3/1987 | Bartholomew |
| 4,906,233 A | | 3/1990 | Moriuchi |
| 5,423,763 A | * | 6/1995 | Helland et al. ............. 604/174 |
| 5,584,874 A | * | 12/1996 | Rugland et al. ............ 607/132 |
| 6,053,902 A | * | 4/2000 | Bestetti et al. ............. 604/523 |
| 6,221,060 B1 | | 4/2001 | Willard |

OTHER PUBLICATIONS

Jorgensen "On–Line" Veterinary Catalog. www.jorvet.com; Chapter XVIII, p. 107, "Jackson Cat Catheter".
Kendall Tyco Healthcare "On–Line" Healthcare Products Catalog. www.kendallhq.com; Vet Medical Catalog, Animal Health Medical Section, Sovereign Sterile Tom Cat Catheters with Non–Slip Suturing Adapter (p. 39).

* cited by examiner

*Primary Examiner*—Brian L. Casler
*Assistant Examiner*—Roz Maiorino

(57) ABSTRACT

The object of this invention is to provide a simple, safe, convenient and economical means of securing catheters to or at the outside of a human or other animal body by suturing, tying or taping to a tubular depression-shaped anchor member that is integrally formed during manufacture with the forming of the catheter resulting in a one-piece multipurpose combination construction unit.

7 Claims, 3 Drawing Sheets

CATHETER WITH INTEGRAL ANCHORING MEANS

CROSS-REFERENCES TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING", A TABLE, OR A COMPUTER PROGRAM LISTING APPENDIX SUBMITTED ON A COMPACT DISC

Not applicable.

BACKGROUND OF THE INVENTION

The present invention relates to a method of use for securing a urethral catheter to or at the outside of a patient's body in order to prevent or restrict undesirable movement or displacement of said catheter while in, on, or at the patient's body. This invention references the following U.S. patent classification/sub classification as the field of endeavor: CLASS 604/174 Surgery/Means for securing conduit to body.

Urethral catheters used in surgical or medical procedures for humans and animals alike usually require attachment to or at the patient's body in order to avoid undesirable tube movement or displacement. A variety of conventional methods are employed to secure a urethral catheter to a patient's body those of which include suturing, taping, strapping, stapling, rubber-banding, using pressure-sensitive adhesive pads or a combination thereof. Of all the preferred methods suturing is the most effective, durable and economical means of attaching urethral catheters to a patient's body.

In order to accommodate the attachment of a suture to a urethral catheter tube or member thereof, many catheter designs use different types of suture retention means that are located on various mating components such as catheter wing members, catheter flange members, catheter collars, catheter hubs, slip on suture pads and grooved tube members.

For example U.S. Pat. No. 3,730,187 to Reynolds reflects a urethral catheter using a tube mounted securing collar that can be sutured to a patient's body. U.S. Pat. No. 3,821,957 to Riley describes a utility catheter with a tube mounted retention slide whose lugs permit suturing to a patient's body. The utility catheter of U.S. Pat. No. 4,230,110 to Beroff comprises a hub section that is suture pierceable allowing suture attachment to a patient's body. The adapter body shown in U.S. Pat. No. 4,650,473 to Bartholomew is a device that fits on the proximal end of a blood vessel catheter and has suture holes at its wing tips and in addition a saddle for looping a suture across and then to a patient's body. The "Tom Cat" urethral catheter made by Kendall Sovereign is supplied with a frictional fit slip-on winged suturing adapter with suture holes that permit suturing to a patient's body. The "Jackson" urehral cat catheter made by Jorgensen Laboratories, Inc. is supplied with a button with holes that serves as an attachment for suture retention to a patient's body. U.S. Pat. No. 4,906,233 to Moriuchi uses a sliding catheter tube sleeve with an annular groove for retaining sutures that will be attached to a patient's body for intravenous use. Prior art U.S. Pat. No. 5,423,763 to Helland and U.S. Pat. No. 5,584,874 to Rugland are suture sleeves that slide over electrical lead catheters.

All of the aforementioned patents use suture type retention devices in order to anchor a catheter tube to a patient's body. However, these suture retention devices are individually constructed components thereby associated with additional manufacturing costs beyond the cost of the catheter tube proper.

Prior art U.S. Pat. No. 6,053,902 to Bestetti teaches a catheter tube with an adiacent suturingrib "welded" to a funnel shaped head on the inlet end and is designed strictly for implantation in a blood vessel of a patient's body and not for urethral insertion. The novel differences between Bestetti and the present invention are that the present invention is designed for urethral insertion and is a solidtary tapered onepiece construction unit from inlet to outlet with no breaks or divisions thus not requiring any additional welding or other steps of manufacture as Bestetti's does as described in his Detailed Deseription in his Specification. Bestetti does not teach a "tapered" catheter tube as the tapering is required to reduce pain in a urethral insertion procedure as the patient is not anesthetized and not undergoing surerg. Bestetti's catheter does not have a tagored outlet portion because the tapering is not required due to the fact that the patient is flirst anesctetized and the catheter is then surgically implanted in a blood vessel.

BRIEF SUMMARY OF THE INVENTION

The obiect of this invention is to provide a simple, safe, convenient and economical method of attaching urethral catheters to or at the outside of a human or other animal body by suturing, tying or taping to a tubular depression-shaped anchor member that is simultaneously and integrally constructively formed with the catheter tube proper durina manufacture resulting in a single one-piece solidtary tapered combination construction unit with no breaks or divisions.

The present invention applies to utral catheter devices constructed of plastic, rubber, glass, metal or other suitable materials. It is intended that this tubular depression-shaped anchor member of the catheter be integrally formed during manufacture with the forming of the overall catheter resulting in a one-piece urethral catheter construction unit. The prior art requires the manufacture and assembly of multiple components in order to produce an equal unit. The novel "built-in" tubular depression-shaped anchor member of this ural catheter obviously requires far less production material than that of the prior art thereby significantly reducing manufacturing costs. Also there are no individual or additional anchoring components to inspect, test, sterilize, package or distribute.

Due to the simplistic design of the present invention, medical personnel will not find it necessary to assemble various parts, hunt for misplaced parts or replace dropped parts. Suturing, tying or taping can irimmediately begin after finalizing catheter placement. This novel tubular depression-shaped anchor member is in very limited contact with the patient's body thus reducing the potential for bacterial growth and infection. The attachment site on or at the body remains visible and accessible at all times and can easily be observed or cleansed. The absence of suture pads, suture buttons and the like allow maximum air circulation to flow around the tubular depression-shaped anchor member. Due to its high visibility medical personnel will be able to readily severe sutures, ties or tape for urethral catheter repositioning or removal.

It is an object of the present invention that the tubular depression-shaped anchor mernber, whether it be configured as an hourglass type shape, a radial collar or a radial groove, that the tubular depression-shaped anor member be capable of retaining sutures, ties, tape or other similar fasteners.

It is also an object of the present invention that the tubular deression-shaped anchor member be used in straight, tapered, flexible or rigid tubing or a combination thereof.

Clearly this method of use is a significant improvement and an advantage over the prior art.

BRIEF DESCRIPTION OF THE SEVERAL VIEWS IF THE DRAWINGS

DETAILED DESCRIPTION OF THE INVENTION

Figure 1:
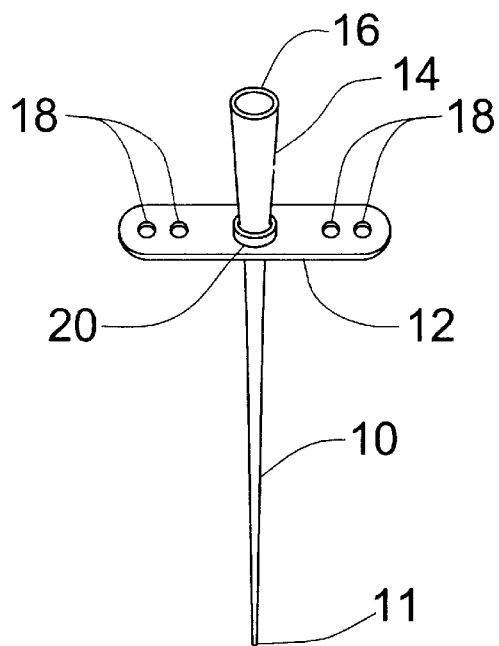
FIG. 1 is a perspective view of the prior art "Tom Cat" urethral catheter.

Prior art FIG. 1 shows a typical "Tom Cat" urethral catheter made by Kendall Sovereign comprised of a semi-rigid polypropylene catheter tube 10 and a flexible polypropylene winged suturing adapter 12. A tapered portion 14 at the proximal end of catheter tube 10 is supplied with an integral female luer end 16 for mounting a syringe or other medical device. Suturing adapter 12 is provided with a plurality of premolded suture holes 18. This two-piece "Tom Cat" catheter design is assembled by slipping distal end 11 of catheter tube 10 through hub 20 which is molded in the center of suturing adapter 12. Hub 20 provides a snug friction fit around tapered portion 14. Once sutures are attached to the patient's body by utilizing suture holes 18, the "Tom Cat" catheter becomes anchored thus avoiding catheter tube movement or displacement. Quite frequently however, the patient's biting and pulling of tapered portion 14 and or luer end 16 causes unwanted movement or removal of catheter tube 10 from the patient's body.

Figure 2:
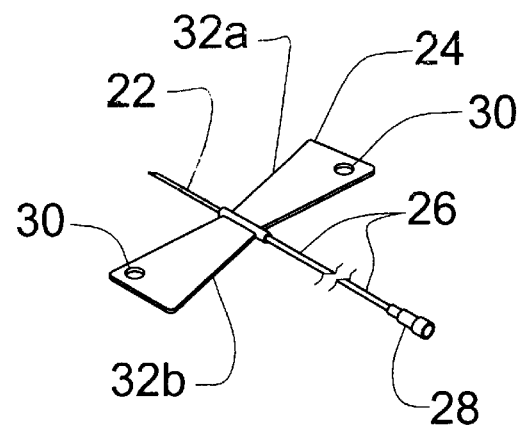
FIG. 2 is a perspective view of the prior art "Butterfly" intravenous catheter.

Prior art FIG. 2 shows a typical "Butterfly" intravenous catheter made by Abbott Laboratories comprised of a steel needle 22, a flexible plastic winged suturing adapter 24 and a flexible length of plastic tube 26. The proximal end of tube 26 is supplied with a female adapter 28 for mounting a syringe or other medical device. Suturing adapter 24 is provided with a plurality of premolded suture holes 30. This four-piece "Butterfly" catheter design is anchored to the patient with sutures by utilizing suture holes 30 or by taping winged portions 32a and 32b to the patient.

Figure 3:
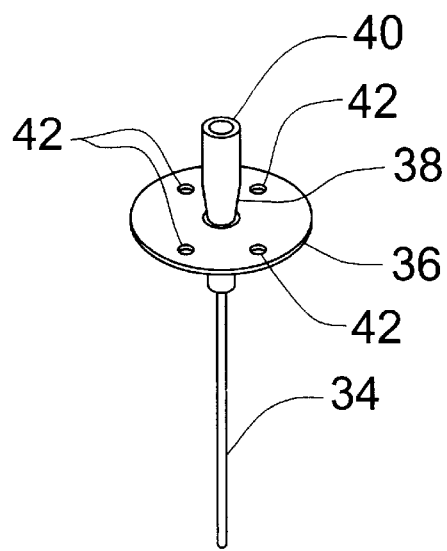
FIG. 3 is a perspective view of the prior art "Jackson" urethral cat catheter.

Prior art FIG. 3 shows a typical "Jackson" urethral cat catheter made by Jorgensen Laboratories, Inc. comprised of a clear nylon catheter tube 34, a nylon tapered portion 38 and a nylon suture button 36. Tapered portion 38 is attached to the proximal end of catheter tube 34 and is supplied with an integral female luer adapter 40 for mounting a syringe or other medical device. Suture button 36 is provided with a plurality of premolded suture retention holes 42. This three-piece "Jackson" catheter design is anchored to the patient with sutures by utilizing suture retention holes 42.

Figure 4:
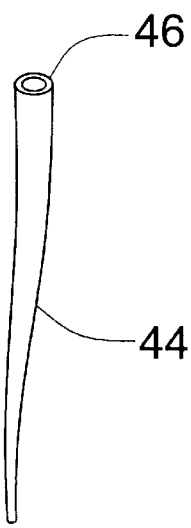
FIG. 4 is a perspective view of a prior art tapered red rubber medical tube that is used as a urethral catheter.

FIG. 4 shows a typical tapered medical tube comprised of a length of flexible tubing 44 and a proximal integral funnel end 46 for mounting a syringe or other medical device. The medical tube shown is tsed as a urethral catheter and is made of medical red rubber tubing material. This one-piece medical tube has no anchoring means and is usually secured by taping the tube to the patient and is quite susceptible to loosening due to fluids.

Figure 5:
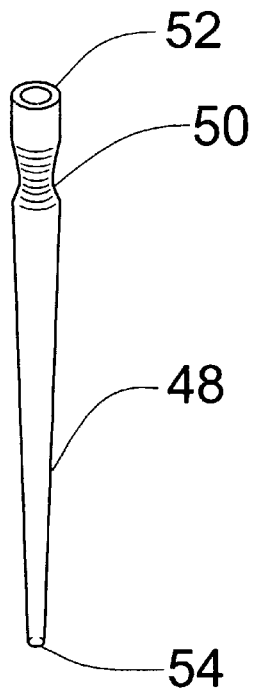
FIG. 5 is aperspective view of the present invention applied to a urethral catheter tube using an hourglass-type shaped anchoring configuration.

FIG. 5 is an example of the present invention and is comprised of a urethral catheter tube 48, a tubular depression-shaped anchor member 50. a proximal integral female luer end 52 and a distal opening 54. The present invention can be made from plastic, rubber, glass, metal or any other suitable material as long as tubular depression-shaped anchor member 50 is integrally formed during manufacture with the forning of catheter tube 48 resulting in a one-piece construction unit. Urethral catheter tube 48 can be tapered or straight or a combination thereof, as well as flexible or rigid. Luer end 52 can be provided as male or female as necessary to accommodate the mounting of syringes or other medical devices. Distal opening 54 can be open-ended or closedended with a lateral opening(s) or combination thereof.

Figure 6:
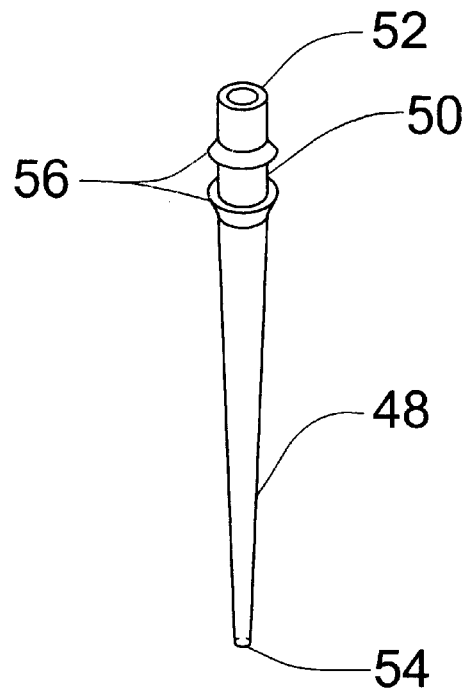
FIG. 6 is a perspective view of the present invention applied to a urethral catheter tube using a radial collar type anchoring design.

The novelty of the present invention is the tubular depression-shaped anchor member 50, which is shown as an hourglass-type shape configuration in FIG. 5. As shown in FIG. 6 tubular depression-shaped anchor member 50 can also be formed with radial collars 56 similar to the radial collars in corrugated tubing, drinking straws and the like. As showvn in FIG. 7 the tubular depression-shaped anchor member can also be formed as a radial groove(s). Not limited to the tubular depression-shaped anchoring configuration designs as shown in urethral catheters FIG. 5, FIG. 6 and FIG. 7, an object of the present invention is that the tubular depression shape formed as the anchor member be able to retain sutures, ties, tape or other similar fasteners and restrict the urethral catheter from longitudinal movement.

Figure 7:
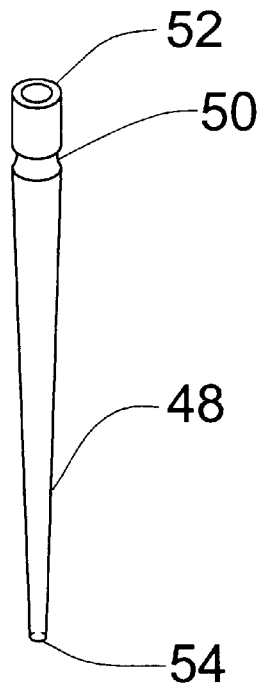
FIG. 7 is a perspective view of the present invention applied to a urethral catheter tube using a radial groove type anchoring design.
Figure 8:
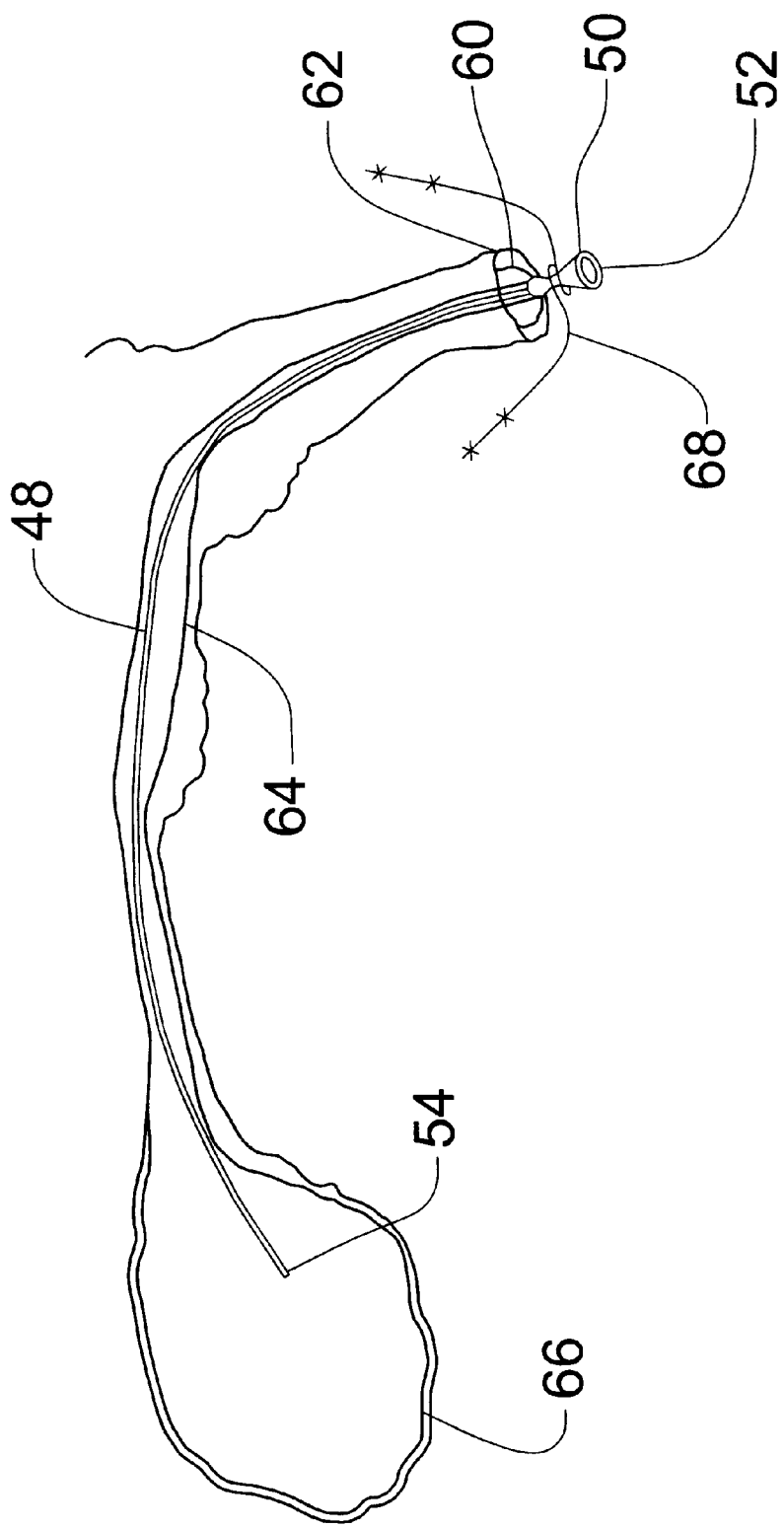
FIG. 8 is a perspective view of the present invention applied to a urethral catheter shown inserted in a feline urethra and sutured to the patient.

FIG. 8 shows an example of the present invention applied to a feline urethral catheter. The feline penis 60 depicted is shown normally sheathed within the prepuce 62. The catheter tube 48 is shown inserted in the urethra 64. Distal opening 54 is shown terminating within bladder 66. Luer end 52 remains outside of the patient's body for mounting a syringe or other medical device. The tubular depression-shaped anchor member 50 has been attached to the paticnt's skin (not shown) with sutures 68 thus restricting longitudinal movement of catheter tube 48. The tubular depression-sbaped anchor member 50 can alternately be suture to prepuce 62 as well. Tubular depression-shaped anchor member 50 is shown here as an hourglass-type shape, but other anchoring configurations such as shown in FIG. 6 and FIG. 7 can be used as weel.

FIG. 8 clearly indicates that a urethral catheter can be simply, safely and economically attached to a patient without the need for any additional costly anchoring components as required and shown in prior art FIG. 1, FIG. 3 and FIG. 4.

We claim:

1. A method of inserting and attaching a urethral catheter for use upon domestic male feline animals comprising the steps of providing a one-piece inseparable catheter tube and anchor member combination unit wherein said catheter tube comprises a proximal end and a distal end, and wherein said catheter tube distal end is elongated and dimensionally variably tapered, and wherein said anchor member is of tubular depression-shaped configuration that provides means for the attachment of sutures and is located adjacent to said proximal end, inserting said catheter tube distal end into said animals' urethra, and suturing said catheter anchor member to said animals' prepuce or prepuce base tissue area thereby preventing the removal or displacement of said catheter tube without also removing said anchor member.

2. The urethral catheter of claim 1 for use upon domestic male canine animals.

3. The urethral catheter of claim 1 for use upon domestic female feline and canine animals wherein said catheter anchor member is sutured to said animals' labia.

4. The urethral catheter of claim 1, claim 2 or claim 3 wherein said catheter anchor member is alternatively sutured to the adjacent epidermal area of the prepuce or prepuce base tissue area, and wherein said catheter anchor member is alternatively sutured to the adjacent epidermal area of the labia.

5. The urttlral catheter of claim 4 whercin said catheter anchor member is alternatively attached by taping, tying or gluing means in lieu of or combined with suturing.

6. The urethral catheter of claim 5 for use upon non-domestic animals including zoological and laboratory animals.

7. The urethral catheter of claim 1 for use upon male and female human patients wherein said catheter distal end is inserted into said humans' urethra and wherein said catheter anchor member is then sutured to said humans' prepuce or prepuce base tissue area, or labia, according to the sex, or adjacent epidermal areas, wherein preventing the removal or displacement of said catheter tube, due to its' novel inseparability from said anchor member, caused by said humans' voluntary or involuntary physical attempts or inadvertent body movement physical forces applied to or about said one-piece inseparable combination unit after said unit has been inserted in said humans' urethra and then sutured in place.

* * * * *